(12) United States Patent
Cavaliere Vesely et al.

(10) Patent No.: US 6,225,104 B1
(45) Date of Patent: May 1, 2001

(54) STRAINS OF BACTERIA AND PHARMACEUTICAL COMPOSITION CONTAINING ONE OR MORE OF SUCH STRAINS AND USE OF SAME FOR PREVENTING AND TREATING DISEASES ASSOCIATED WITH OR CAUSED BY ALTERED METABOLISM OF BILE ACIDS

(76) Inventors: Renata Maria Anna Cavaliere Vesely, Via S. Orsola, 11, Milan; Claudio De Simone, Via Nuoro, 10, Ardea, both of (IT)

(*) Notice: Subject to any disclaimer, the term of this patent is extended or adjusted under 35 U.S.C. 154(b) by 0 days.

(21) Appl. No.: 08/813,776

(22) Filed: Mar. 7, 1997

(30) Foreign Application Priority Data

Mar. 11, 1996 (IT) ............................... MI96A0468

(51) Int. Cl.$^7$ ............................... C12N 1/20; C12N 1/12; A61K 38/16; A61K 38/00
(52) U.S. Cl. ............... 435/252.1; 435/243; 435/252.9; 435/253.4; 435/260; 514/12; 424/178.1
(58) Field of Search ............... 424/178.1; 435/252.9, 435/260, 252.1, 253.4, 243; 514/12

(56) References Cited

U.S. PATENT DOCUMENTS

| | | | |
|---|---|---|---|
| 4,565,811 | * | 1/1986 | Di Schiena . |
| 5,079,240 | * | 1/1992 | Hofmann . |
| 5,707,854 | * | 1/1998 | Saito et al. . |
| 5,716,615 | * | 2/1998 | Cavaliere et al. . |
| 5,895,648 | * | 4/1999 | Cavaliere et al. . |

FOREIGN PATENT DOCUMENTS

| | | | |
|---|---|---|---|
| 0 117 570 | | 9/1984 | (EP) . |
| 0 671 468 | | 9/1995 | (EP) . |
| 0671468 A1 | * | 9/1995 | (EP) . |
| 0795604 A2 | * | 9/1997 | (EP) . |
| 0795604 A3 | * | 4/1998 | (EP) . |
| WO 94/02503 | | 2/1994 | (WO) . |

OTHER PUBLICATIONS

Salvioli et al, Digestion, 23:80–88, 1982.*
Clayton, J. Inherit. Metab. Dis. 14: 478–496, 1991.*
Hill et al, Gut, 9:22–27, 1968.*
Lewis et al Arch. Intern. Med. 130:545–49, Oct. 1972.*
Masuda, Microbiol. Immunol. 25/1: 1–11, 1981.*
Hirano et al, Appl. & Environ. Microbiol. 41/3: 737–745, 1981.*
Masuida et al Appl. & Environ. Microbiol. 45/1: 308–309, 1983.*
Masuida et al Appl. & Environ. Microbiol 45/2: 456–62, 1983.*
Bartizal et al., Lipids 17/11: 791–797, 1982.*
Takamine et al, Microbiol. Immunol 39/1: 11–18, 1995.*
Hirano et al, J. Lipid Research. 23:1152–1158, 1982.*
Takahashi et al, J. DiaryScience 77: 3275–86, 1994.*
P. Marteau, et al., Microbial Ecology in Health and Disease, Vol. 8, pp. 151–157, 1995, "Metabolism Of Bile Salts By Alimentary Bacteria During Transit In The Human Small Intestine".
Takuya Takahashi, et al., Journal of Dairy Sci., vol. 77, No. 11, pp. 3275–3286, 1994, "Absence Of Cholic Acid 7α–Dehydroxylase Activity In The Stains Of Lactobacillus and Bifidobacterium".
G. Salvioli, et al., Digestion, vol. 23, pp. 80–88, 1982, "Bile Acid Transformation By The Intestinal Flora And Cholesterol Saturation In Bile".
James P. Coleman, et al., Journal of Bacteriology, vol. 169, No. 4, pp. 1516–1521, Apr. 1987, "Molecular Cloning Of Bile Acid 7–Dehdroxylase From E*Eubacterium* Sp. Strain VPI 12708".
G. Paumgartner, et al., Falk Sympisium 29, pp. 180–183, 1980, "Bile Acids and Lipids".
T.A. Brasitus, Gastroenterology, vol. 109, No. 6, pp. 2036–2038, 1995, "Primary Chemoprevention Strategies For Colorectal Cancer: Ursodeoxycholic Acid and Other Agents".
D. Kuerktschiev, et al., Journal of Hepatology, vol. 18, pp. 373–377, 1993, "Immunomodulating Effect Of Ursodeoxycholic Acid Therapy In Patients With Primary Biliary Cirrhosis".

* cited by examiner

Primary Examiner—Nita Minnifield
(74) Attorney, Agent, or Firm—Oblon, Spivak, McClelland, Maier & Neustadt, P.C.

(57) ABSTRACT

Strains of bacteria characterized by exhibiting: (a) a 7α-dehydroxylase activity of less than 50%, and (b) a bile acid deconjugation activity of less than 50%, and descendants, mutants and derivatives thereof preserving activities (a) and (b); and a pharmaceutical composition using one or more of such strains and use of same for preventing and treating diseases associated with or caused by an altered metabolism of bile acids.

11 Claims, No Drawings

STRAINS OF BACTERIA AND PHARMACEUTICAL COMPOSITION CONTAINING ONE OR MORE OF SUCH STRAINS AND USE OF SAME FOR PREVENTING AND TREATING DISEASES ASSOCIATED WITH OR CAUSED BY ALTERED METABOLISM OF BILE ACIDS

BACKGROUND OF THE INVENTION

1. Field of the Invention

The present invention relates to strains of bacteria and pharmaceutical compositions containing one or more of such strains and the use of same for preventing and treating diseases associated with or caused by an altered metabolism of bile acids.

2. Discussion of the Background

Hepatic bile is a pigmented isotonic fluid with an electrolyte composition resembling blood plasma. Major components of bile include water (82 percent), bile acids (12 percent), lecithin and other phospholipids (4 percent), and unesterified cholesterol (0.7 percent). Other constituents include conjugated bilirubin, proteins, electrolytes, mucus and the final products of hepatic transformation of drugs, hormones, etc. The liver production of bile, in basal conditions, is approximately 500–1000 ml/day.

The primary bile acids, cholic acid (CA) and chenodeoxycholic acid (CDCA), are synthesized from cholesterol in the liver, conjugated with glycine or taurine, and excreted into the bile. Secondary bile acids, including deoxycholic acid (DCA) and lithocholic acid (LA), are formed in the colon as bacterial metabolites of the primary bile acids. Other bile acids, called tertiary bile acids (e.g.: ursodeoxycholic acid—UDCA), are formed in the gut following the enzymatic epimerization of —OH groups on sterol rings by the intestinal flora.

In normal bile, the ratio of glycine to taurine conjugates is about 2:1, while in patients with cholestasis, increased concentrations of sulfate and glucuronide conjugate of bile acids are often found. The intestinal microflora transforms the bile acids into different metabolites. These biotransformations include the hydrolysis of the bond between the bile acid and taurine or glycine, with formation of unconjugated or free bile acids and taurine or glycine. The unconjugated bile acids are therefore made available for the oxidation of the hydroxylic groups in positions C3, C7, and C12 and for the dehydroxylation in positions $7\alpha$ and $7\beta$. This latter transformation leads to the formation of the secondary bile acids DCA and LA. The primary bile acids, deconjugated bile not transformed, and the secondary biliary acids are reabsorbed from the gut lumen and enter the portal bloodstream, then are taken up by hepatocytes, conjugated with glycine or taurine and resecreted into the bile (enterohepatic circulation).

Normally, the bile acid pool circulates approximately 5 to 10 times daily. Intestinal absorption of the pool is about 95% efficient, so fecal loss of bile acids is in the range of 0.3 to 0.6 g/day. The fecal loss is compensated by an equal daily synthesis.

For this reason the composition of the pool of biliary acids present in the bile is the result of complex interactions occurring between the liver and the microflora enzymes.

Deconjugation activity is a characteristic shared by many bacteria, aerobes and anaerobes, but is particularly common among the obligate anaerobic bacteria, i.e. Bacteroides, Eubacteria, Clostridia, Bifidobacteria, etc. The majority of the bacteria is active against both glycine and taurine conjugates; however, some of them have a certain degree of specificity, depending on the bound amino acid and the number of hydroxides bound to the steroid nucleus. The free biliary acids obtained following the action of the bacterial hydrolases can undergo the oxidation of the hydroxide groups present at the C3, C7, and C12 positions by the hydroxysteroidodehydrogenase.

The interest in the metabolic disorders of biliary acids comes from the hypothesis that biliary acids and/or metabolites thereof are involved in the pathogenesis of some hepato-biliary and gastroenterologic diseases: biliary dyspepsia, cholelithiasis, acute and chronic hepatopathies, inflammatory diseases of the colon, etc.

Very often in literature the hydrophobicity of the bile acid is correlated with detergency; the secondary bile acids are more hydrophobic than the primary bile acids, the deoxycholic acid (DCA) being actually more detergent than the cholic acid (CA). Therefore an increased concentration of DCA in the bile may involve: a) an augmentation of the secretion of cholesterol, with increased saturation index; b) a cytotoxic effect on the liver cells.

For this reason a qualitative modification of the bile acids pattern could be a decisive factor, especially in treating the above-mentioned pathologies.

Thus, there remains a need for effective bacterial strains or compositions that, by reducing the $7\alpha$-dehydroxylase activity and at the same time deconjugation, can be used for treating and/or preventing diseases associated with metabolic disorders of the biliary acids.

No bacteria strains have been found that are capable of qualitatively modifying the bile acid pattern in such a way.

SUMMARY OF THE INVENTION

Accordingly, it is one object of the present invention to provide novel strains of bacteria, in particular gram-positive bacteria, which are useful for treating and/or preventing diseases associated with or caused by a metabolic disorder of biliary acids.

It is another object of the present invention to provide pharmaceutical compositions which contain one or more strains of such bacteria and are useful for treating and/or preventing diseases associated with or caused by a metabolic disorder of biliary acids.

It is another object of the present invention to provide a novel method for treating and/or preventing diseases associated with or caused by a metabolic disorder of biliary acids.

The foregoing and other objects, which will become more apparent during the following detailed description, have been achieved by the inventors, who have found bacteria strains having a reduced or zero $7\alpha$-dehydroxylase activity and a reduced or zero ability to deconjugate bile acids. This is in contrast with the previous known art. Accordingly, the present invention provides the use of such strains to modify the bile acid metabolism in a useful manner to prevent or treat diseases caused by or associated with metabolic disorders of biliary acids.

DETAILED DESCRIPTION OF THE PREFERRED EMBODIMENTS

Thus, in a first embodiment, the present invention provides novel strains of bacteria which have a $7\alpha$-dehydroxylase activity of less than 50%, preferably less than 25%, and a conjugated bile acid deconjugation activity of less than 50%, preferably less than 25%.

The strains according to the present invention are gram-positive bacteria strains characterized by exhibiting: (a) a $7\alpha$-dehydroxylase activity of less than 50%, and (b) a bile acid deconjugation activity of less than 50%, and belonging to a species selected from *Streptococcus thermophilus* and *Lactobacillus bulgaricus*.

Specific strains having said features are:

*Streptococcus thermophilus* YS 52;

*Streptococcus thermophilus* YS 46;

*Streptococcus thermophilus* YS 48;

*Lactobacillus bulgaricus* LB 1;

*Lactobacillus bulgaricus* LB 3;

*Lactobacillus bulgaricus* LB 7;

*Lactobacillus bulgaricus* LB 77.

All of the above mentioned strains are deposited with the CNCM, Collection Nationale de Cultures de Microorganismes, Institut Pasteur, with the accession number specified in Table II.

The present invention also provides a pharmaceutical composition for treating and/or preventing diseases associated with or caused by an altered metabolism of biliary acids, said composition comprising at least one bacteria strain according to the present invention.

The compositions for preventing and/or treating diseases associated with or caused by an altered metabolism of bile acids according to the present invention comprise an effective amount capable of producing a normalizing effect in a patient suffering therefrom of (1) at least one gram-positive bacteria strain characterized by exhibiting: (a) a 7α-dehydroxylase activity of less than 50%, and (b) a bile acid deconjugation activity of less than 50%, and belonging to a species selected from *Streptococcus thermophilus* and *Lactobacillus bulgaricus;* and (2) a pharmaceutically acceptable carrier.

Specific strains for the present compositions are:

*Streptococcus thermophilus* YS 52;

*Streptococcus thermophilus* YS 46;

*Streptococcus thermophilus* YS 48;

*Lactobacillus bulgaricus* LB 1;

*Lactobacillus bulgaricus* LB 3;

*Lactobacillus bulgaricus* LB 7;

*Lactobacillus bulgaricus* LB 77.

In another embodiment, the present invention provides a method for treating and/or preventing diseases caused by or associated with an altered metabolism of biliary acids by administering to a patient in need thereof one or more strains of bacteria which have a 7α-dehydroxylase activity of less than 50%, preferably less than 25%, and a conjugated bile acid deconjugation activity of less than 50%, preferably less than 25%, or a pharmaceutical composition containing one or more such strains of bacteria.

The method according to the present invention for preventing and/or treating diseases caused by or associated with an altered metabolism of bile acids, comprises administering at least one gram-positive bacteria strain characterized by exhibiting: (a) a 7α-dehydroxylase activity of less than 50%, and (b) a bile acid deconjugation activity of less than 50%, and belonging to a species selected from *Streptococcus thermophilus* and *Lactobacillus bulgaricus*.

Specific strains for the present method are:

*Streptococcus thermophilus* YS 52;

*Streptococcus thermophilus* YS 46;

*Streptococcus thermophilus* YS 48;

*Lactobacillus bulgaricus* LB 1;

*Lactobacillus bulgaricus* LB 3;

*Lactobacillus bulgaricus* LB 7;

*Lactobacillus bulgaricus* LB 77.

In the context of the present invention, the diseases associated with or caused by a metabolic disorder of the biliary acids include liver diseases and diseases of the digestive apparatus, such as blind loop syndrome, biliary gallstones, cirrhosis, chronic hepatopathies, acute hepatopathies, cystic fibrosis, intrahepatic cholestasis, intestinal inflammatory diseases, colonpathies, malabsorption. The present pharmaceutical compositions may also be used to prevent the onset of biliary gallstones in women during pregnancy or subsequent periods and in subjects undergoing weight-loss programs or diets.

The 7α-dehydroxylase activity of the bacteria strain should be less then 50%, preferably less than 25%. The 7α-dehydroxylase activity values are those measured by the method described in Example 1 below. Specifically, the $10^7$ cells of the strain in question are incubated at 37° C. for 48 hours, in 15 ml of the specific culture medium with the addition of 2 mg/ml of glycocholic acid (GCA) or 2 mg/ml of taurocholic acid (TCA), and then the amount of 7α-dehydroxylated product is measured. The percentage value for the 7α-dehydroxylase activity is calculated by the following formula:

$$7\alpha\text{-dehydroxylase activity} = \frac{\text{mass of } 7\alpha\text{-dehydroxylated product after 48 hours of incubation}}{\text{mass of GCA or TCA at the start of incubation}} \times 100$$

The 7α-dehydroxylase activity for any given strain is the higher of the numbers measured for GCA and TCA.

Based on the above, the bacteria strain to be administered should in addition have a conjugated bile acid deconjugation activity of less than 50%, preferably less than 25%. The ability to deconjugate bile acid is determined by using the same incubation procedure described for measuring the 7α-dehydroxylase activity followed by measuring the amount of deconjugated product formed. The deconjugation activity is calculated using the following formula:

$$\text{Deconjugation activity} = \frac{\text{mass of deconjugated GCA or TCA after 48 hours of incubation}}{\text{mass of GCA or TCA at the start of incubation}} \times 100$$

The deconjugation activity for any given strain is the higher of the numbers measured for GCA and TCA.

The bacteria strains of the present invention may be administered enterically. Preferably, the bacteria strains of the present invention are administered orally.

Although a single bacteria strain may be administered, it is also possible to administer a mixture of two or more bacteria according to the present invention.

Although the exact dosage of bacteria to be administered will vary with the condition and size of the patient, the exact disease being treated, and the identity of the strains being administered, good results have been achieved by administering $10^3$ to $10^{13}$ cells of the bacteria/g, preferably $10^8$ to $10^{12}$ of the bacteria strain/g. To achieve the good effects of the present invention, it is preferred that the strain be administered in an amount and a concentration sufficient to result in the intestines of the patient being populated with an important amount thereof. Thus, it is preferred that the strain be administered in a composition which contains $10^3$ to $10^{13}$ cells of the strain/g, preferably $10^8$ to $10^{12}$ cells of the strain/g and that the composition be administered in such a regimen so that the patient receives 100 mg to 100 g of the strain/day, preferably 1 g to 20 g of the strain/day, for a period of 1 to 365 days, preferably 3 to 60 days in case of therapy, or according to periodical cycles in case of prophylaxis. The bacteria strain may be administered in any form suitable for enteral administration, such as capsules, tablets, or liquids for oral administration or liquids for enteral administration.

Typically, the administration of the bacteria strain according to the present invention can be prescribed after the diagnosis of metabolic disorders of the biliary acids. However, in the case of the prophylaxis of biliary gallstones, the strain may be administered when the subject is determined to belong to an at-risk population, such as becoming pregnant or beginning a weight-loss program or diet. In addition, the present strain of bacteria may be administered after a patient has had their gallbladder removed.

In a preferred embodiment, the coadministration of lactulose is provided when the disease being treated is cirrhosis. Suitably, the lactulose is administered in an amount of 100 mg to 100 g/day, preferably 1 g to 20 g/day.

In another preferred embodiment, the coadministration of bile acid-based preparations, such as ursodeoxycholic acid or tauroursodeoxycholic acid, is provided. Suitably, the ursodeoxycholic or tauroursodeoxycholic acid is administered in an amount of 10 to 3,000 mg/day, preferably 50 to 800 mg/day.

The present invention finally provides novel pharmaceutical compositions for treating and/or preventing the metabolic disorders of the biliary acids which comprise (a) one or more strains of bacteria having a 7α-dehydroxylase activity of less than 50%, preferably less than 25%, and a bile acid deconjugation activity of less than 50%, preferably less than 25%, and (b) a pharmaceutically acceptable carrier. Preferably, the present pharmaceutical compositions contain the strain(s) of bacteria in a concentration of $10^3$ to $10^{13}$ cells/g, preferably $10^8$ to $10^{12}$ cells/g. The pharmaceutically acceptable carrier may be any which is suitable for enteral administration and is compatible with the strain of bacteria, such as dextrose, calcium carbonate together with different additional substances such as starch, gelatin, vitamins, antioxidants, stains or taste-improving substances.

As an optional component, the compositions of the invention may possibly contain a drug compatible with the bacteria employed and capable of potentiating the activity of the active ingredients present. Anticholinergic drugs, antihistamines, adrenergic, antiulcer, antiacid, antidiarroic, and anti-inflammatory drugs, sedatives, antipyretis, choleretics antirheumatic agents, analgesic drugs, diuretics, antiseptic agents, antilipemic hepatoprotective drugs and drugs active on the gastrointestinal motility (e.g., trimebutine) may be herein mentioned.

When treating cirrhosis, it is preferred that the pharmaceutical composition further comprise lactulose. Suitably, the composition will contain sufficient lactulose to result in the administration of 100 mg to 100 g/day, preferably 1 g to 20 g/day of lactulose. When treating biliary cirrhosis and chronic hepatitis, it is preferred that the pharmaceutical composition comprise bile acid-based preparations, such as ursodeoxycholic acid or tauroursodeoxycholic acid. Suitably, the composition will contain sufficient bile acid preparation to result in the administration of 10 to 3,000 mg/day of such bile acid preparations, preferably 50 to 800 mg/day of ursodeoxycholic acid or tauroursodeoxycholic acid.

Other features of the invention will become apparent in the course of the following descriptions of exemplary embodiments which are given for illustration of the invention and are not intended to be limiting thereof.

EXAMPLES

Example 1

Strains of the following species have been tested: *Streptococcus thermophilus, Streptococcus faecium, Lactobacillus acidophilus, Lactobacillus bulgaricus, Lactobacillus plantarum, Bifidobacterium infantis*. Each strain ($10^7$ CFU) was cultivated in duplicate in specific nutrient broths (15 ml); "CFU" means "colony forming units".

List of the Employed Culture Media Depending on the Different Species

| | |
|---|---|
| *Bifidobacterium infantis*: | MRS + 0.5% glucose (added after sterilization by diluting a 20% sterile solution) |
| *Streptococcus thermophilus*: | M17 |

*Streptococcus thermophilus:* M17
All the Remaining Strains MRS
Composition of the MRS Broth

| | | |
|---|---|---|
| g/liter | universal peptone | 10.0 g |
| | meat extract | 5.0 g |
| | yeast extract | 5.0 g |
| | D(+)-glucose | 20.0 g |
| | potassium hydrogen phosphate | 2.0 g |
| | Tween 80 | 1.0 g |
| | dibasic ammonium citrate | 2.0 g |
| | sodium acetate | 5.0 g |
| | magnesium sulfate | 0.1 g |
| | manganous sulfate | 0.05 g |

Preparation: dissolve 50 g/l in distilled water, sterilized at 121° C. for 15 minutes—pH 6.5±0.1 at 25° C.
Composition M17 Broth (Merck)

| | | |
|---|---|---|
| g/liter | soybean flour peptone | 5.0 g |
| | meat peptone | 2.5 g |
| | casein peptone | 2.5 g |
| | yeast extract | 2.5 g |
| | meat extract | 5.0 g |
| | D(+)-lactose | 5.0 g |
| | ascorbic acid | 0.5 g |
| | sodium-β-glycerophosphate | 19.0 g |
| | magnesium phosphate | 0.25 g |

Preparation: dissolve 42.5 g/l in distilled water, sterilized at 121° C. for 15 minutes . pH 7.2±0.1 at 25°

*Bifidobacterium infantis* was cultivated under anaerobic conditions since it is known that it is an anaerobic bacterium. After 24 hours of incubation at 37° C. to each tube was added an amount of bile salt equivalent to 30 mg in order to obtain a final concentration of 2 mg/ml. The bile acids employed are: glycocholic acid (GCA) and taurocholic acid (TCA), obtained from Sigma Chemicals. Each bile acid was added separately to each series of bacterial cultures.

After 48 hours of incubation, isopropanol, 3 ml, was added for 2 minutes. Then it was centrifuged at 400 rpm for 15 minutes and the supernatant was collected (5 ml). The supernatant was kept refrigerated at −30° C. until it was analyzed. The percentage of conjugated bile salt present was determined by HPLC (high performance liquid chromatography) utilizing a Gilson apparatus equipped with a detector Diode array mod 1000 and a Spherisorb 5 μm ODS 2 C18 reverse phase column, a mobile phase composed by methanol/buffered phosphate (20 mMol), pH 2.5 in water/acetonitrile/water (150:60:20:20 by volume), a fluid speed of 0.85 ml/min, at a wavelength of 205 nm; 100 μl of the sample to be tested, dried under nitrogen, were extracted with 100 μl of the mobile phase containing as an internal standard 7α-OH-12α-OH-dihydroxy-5ß-cholanic acid (Calbiochem U.S.A.) at a concentration of 2 mg/ml.

The recovery percentage of the bile acid incubated with the bacterial cultures was calculated by the ratio of the area of the bile acid to be detected (GCA or TCA) to the area of the internal standard. When the quantity of the conjugated bile acid found in the bacterial cultures after 48 hours of incubation was less than 50%, thin layer chromatography (TLC) was performed on silica 60 gel plates to detect the presence of CA and DCA, using a mobile phase of cyclohexane/isopropanol/acetic acid (30:10:1 by volume). On every plate, 20 μl of the alcoholic extract of the sample, 20 μl of a solution of CA and DCA, and 20 μl of CA, 20 μl of DCA, were spotted. The plates after development at room temperature, were treated with sulfuric acid and warmed at 145° C. until the appearance of the colored spots.

The results of the deconjugation experiments (Table I) show that 5 out of the 16 strains tested with GCA were able to completely deconjugate the bile acid added to the culture, as previously reported in the literature and widely known to all researchers. Surprisingly, ten strains were able to deconjugate GCA but not completely, ranging from 9 to 90 percent (Table I). There was no difference among aerobic and anaerobic bacteria. Two strains, *Streptococcus thermophilus* YS 52 and *Bifidobacterium infantis* Bi 6 do not have any deconjugating activity for GCA. The strain YS 52 in addition does not attack the bile acid-taurine bond.

Only one out of the 16 strains tested was able to totally deconjugate the TCA: the *Bifidobacterium infantis* Bi 6.

The results of the dehydroxylation experiments (Table II) show that only one (Bi 4) out of the 16 strains is able to completely dehydroxylate GCA. Six strains did not dehydroxylate at all: YS 52; SF 2; SF 4; LA 3; LA 10; and Bi 6. The other strains were able to dehydroxylate GCA but not completely, ranging from 9% to 90%. As to TCA, seven strains do not dehydroxylate it at all: YS 52; SF 3; LA 3; LA 10; LB 1; LB 7; and LB 77. One strain, Bi 6, dehydroxylated TCA completely; the other strains dehydroxylated TCA according to varying percentages.

TABLE I

Percentage of deconjugation of GCA and TCA by bacterial cultures after 48 hours of incubation

| BACTERIUM | ACCESSION NO. | GCA % | TCA % |
|---|---|---|---|
| *Streptococcus thermophilus* YS 46 | I-1668 | 9 | 9 |
| *Streptococcus thermophilus* YS 48 | I-1669 | 17 | 11 |
| *Streptococcus thermophilus* YS 52 | I-1670 | 0 | 0 |
| *Streptococcus faecium* SF 2 | | 100 | 3 |
| *Streptococcus faecium* SF 3 | I-1671 | 27 | 0 |
| *Streptococcus faecium* SF 4 | | 100 | 12 |
| *Lactobacillus acidophilus* LA 3 | | 100 | 80 |
| *Lactobacillus acidophilus* LA 10 | | 100 | 95 |
| *Lactobacillus bulgaricus* LB 1 | I-1664 | 9 | 0 |
| *Lactobacillus bulgaricus* LB 3 | I-1665 | 20 | 12 |
| *Lactobacillus bulgaricus* LB 7 | I-1666 | 14 | 0 |
| *Lactobacillus bulgaricus* LB 77 | I-1667 | 20 | 0 |
| *Bifidobacterium infantis* Bi 2 | | 80 | 15 |
| *Bifidobacterium infantis* Bi 3 | | 90 | 10 |
| *Bifidobacterium infantis* Bi 4 | | 100 | 26 |
| *Bifidobacterium infantis* Bi 6 | | 0 | 100 |

TABLE II

Percentage of dehydroxylation of GCA and TCA by bacterial cultures after 48 hours of incubation

| BACTERIUM | ACCESSION NO. | GCA % | TCA % |
|---|---|---|---|
| *Streptococcus thermophilus* YS 46 | I-1668 | 9 | 9 |
| *Streptococcus thermophilus* YS 48 | I-1669 | 17 | 11 |
| *Streptococcus thermophilus* YS 52 | I-1670 | 0 | 0 |
| *Streptococcus faecium* SF 2 | | 0 | 3 |
| *Streptococcus faecium* SF 3 | I-1671 | 27 | 0 |
| *Streptococcus faecium* SF 4 | | 0 | 12 |
| *Lactobacillus acidophilus* LA 3 | | 0 | 0 |

TABLE II-continued

Percentage of dehydroxylation of GCA and TCA by bacterial cultures after 48 hours of incubation

| BACTERIUM | ACCESSION NO. | GCA % | TCA % |
|---|---|---|---|
| *Lactobacillus acidophilus* LA 10 | | 0 | 0 |
| *Lactobacillus bulgaricus* LB 1 | I-1664 | 9 | 0 |
| *Lactobacillus bulgaricus* LB 3 | I-1665 | 20 | 12 |
| *Lactobacillus bulgaricus* LB 7 | I-1666 | 14 | 0 |
| *Lactobacillus bulgaricus* LB 77 | I-1667 | 20 | 0 |
| *Bifidobacterium infantis* Bi 2 | | 80 | 15 |
| *Bifidobacterium infantis* Bi 3 | | 90 | 10 |
| *Bifidobacterium infantis* Bi 4 | | 100 | 26 |
| *Bifidobacterium infantis* Bi 6 | | 0 | 100 |

These strains have been deposited with the CNCM, Collection Nationale de Cultures de Microorganismes, Institut Pasteur, 28 rue du Dr Roux, 75724 Paris Cédex 15, France, under the following accession numbers:
*Streptococcus thermophilus* YS 46: I-1668
*Streptococcus thermophilus* YS 48: I-1669
*Streptococcus thermophilus* YS 52: I-1670
*Streptococcus faecium* SF 3: I-1671
*Lactobacillus bulgaricus* LB 1: I-1664
*Lactobacillus bulgaricus* LB 3: I-1665
*Lactobacillus bulgaricus* LB 7: I-1666
*Lactobacillus bulgaricus* LB 77: I-1667

The following strains are on the contrary kept at the Centro Ricerche Sitia-Yomo S.p.A., —strada per mercino 3-ZELO BUON PERSICO (MILAN)—ITALY, distinguished by the below-reported identifiers:
*Streptococcus faecium* SF 2: SF 2
*Streptococcus faecium* SF 4: SF 4
*Lactobacillus acidophilus* LA 3: LA 3
*Lactobacillus acidophilus* LA 10: LA 10
*Bifidobacterium infantis* Bi 2: Bi 2
*Bifidobacterium infantis* Bi 3: Bi 3
*Bifidobacterium infantis* Bi 4: Bi 4
*Bifidobacterium infantis* Bi 6: Bi 6

These results demonstrate that the majority of the strains tested by us have a low capability to deconjugate the bile acids and that there are strains that do not deconjugate at all. This observation is surprising in that it has not been known that the lactic acid bacteria deconjugated the biliary salts. Furthermore, it is evident that the enzymes of the strains are selective for the specific bile acid bound on the side chain. In this study, the clearest example is offered by the *Bifidobacterium infantis* Bi 6. This strain is not able to deconjugate the glycine-conjugated bile acid but is able to totally deconjugate the taurine-conjugated bile acid. Some other strains (LB 1, LB 7, LB 77, and SF 3) are unable to deconjugate TCA but are able to deconjugate GCA to a certain extent.

To conclude, strains have been discovered that have a weak or zero capability to deconjugate and dehydroxylate.

Example 2

Three healthy volunteers were tested for their content of bile acids following treatment with a lactobacilli preparation containing $1 \times 10^{11}$ cells of *Streptococcus thermophilus* YS 52 per gram for a daily total of 6 g for 28 days. Before beginning the treatment and after 12 hours starvation, the subjects were intubated and the gallbladder bile, following stimulation with ceruletide, was collected and frozen at −80° C. The gallbladder contraction was assessed by echography and the position of the tube, in the second portion of the duodenum was checked by Rx (fluoroscopy).

After a 4 week treatment, the subjects underwent a second intubation and collection of bile. The bile samples were then tested for their content of some bile acids as previously described. The results are shown in Table III.

TABLE III

| Bile Acid | Patient #1 | | Patient #2 | | Patient #3 | |
|---|---|---|---|---|---|---|
| | Before | After | Before | After | Before | After |
| Glychenodeoxycholic | 32 | 15 | 22 | 15 | 28 | 12 |
| Glycodeoxycholic | 6 | 5 | 9 | 2 | 4 | 3 |
| Glycoursodeoxycholic | 1 | 5 | 1 | 7 | 1 | 4 |
| Taurocholic | 9 | 26 | 15 | 25 | 12 | 21 |
| Taurodeoxycholic | 1 | 3 | 5 | 8 | 3 | 9 |

NOTE: (the bile acids are listed following the hydrophilic capacity order, that is in inverse relation to detergency)
Taurocholic
Taurodeoxycholic
Glycoursodeoxycholic
Glycodeoxycholic
Glychenodeoxycholic This experiment is a confirmation of what is shown in Example No. 1, that is: a lower deconjugation in one of the primary bile acids if bacteria being the object of the present invention are administered. The achieved result is a longer maintenance of the primary bile acids in the enterohepatic circulation.

The properties of the bile acids are reported in the note to Table III. Thus, according to these results the administration of selected strains of bacteria can reduce the detergency property and therefore the cytolytic activity of the bile acids.

Example 3

Fourteen patients with chronic hepatitis were treated with a bacterial preparation containing Streptococcus thermophilus YS 46 and YS 48 (two strains), and Lactobacillus bulgaricus LB 1, LB 7, and LB 77 (three strains). Each strain had been brought to a concentration of $150 \times 10^9$ cells per gram before being mixed with the others, to prepare a mixture containing the same parts by weight of each strain. 6 grams per day of said mixture were administered for 28 days. Liver enzymes were measured before and after the treatment, and the results are shown in Table IV.

TABLE IV

Influence of the Treatment with the Bacterial Mixture on Liver Enzymes Aspartate Transaminase (AST; SGOT) and alanine transaminase (ALT; SGPT)

| Patient | AST (SGOT) | | ALT (SGPT) | |
|---|---|---|---|---|
| | Before | After | Before | After |
| #1 | 92 | 59 | 102 | 46 |
| #2 | 89 | 67 | 96 | 42 |
| #3 | 174 | 86 | 97 | 39 |
| #4 | 121 | 91 | 102 | 66 |
| #5 | 116 | 81 | 111 | 55 |
| #6 | 156 | 87 | 94 | 76 |
| #7 | 163 | 66 | 69 | 37 |
| #8 | 78 | 64 | 122 | 57 |
| #9 | 109 | 39 | 87 | 86 |
| #10 | 166 | 70 | 102 | 48 |
| #11 | 56 | 24 | 118 | 62 |
| #12 | 131 | 83 | 96 | 79 |
| #13 | 137 | 86 | 94 | 74 |
| #14 | 84 | 87 | 144 | 114 |
| Mean | 119 | 71 | 102 | 63 |
| Standard deviation | 36 | 19 | 17 | 21 |
| Significance Student t test for paired data | $p < 0.001$ | | $p < 0.001$ | |

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by Letters Patent of the United States is:

1. A biologically pure gram-positive bacteria strain characterized by exhibiting:

(a) a 7α-dehydroxylase activity of less than 50%, and (b) a bile acid deconjugation activity of less than 50%, and belonging to a species selected from Streptococcus thermophilus and Lactobacillus bulgaricus, wherein said strain modifies bile acid metabolism.

2. The biologically pure strain of claim 1, wherein the bacteria strain is Streptococcus thermophilus YS 52, deposited with the CNCM, Collection Nationale de Cultures de Microorganismes, Institut Pasteur, under the accession number I-1670.

3. The biologically pure strain of claim 1, wherein the bacteria strain is Streptococcus thermophilus YS 46, deposited with the CNCM, Collection Nationale de Cultures de Microorganismes, Institut Pasteur, under the accession number I-1668.

4. The biologically pure strain of claim 1, wherein the bacteria strain is Streptococcus thermophilus YS 48, deposited with the CNCM, Collection Nationale de Cultures de Microorganismes, Institut Pasteur, under the accession number I-1669.

5. The biologically pure strain of claim 1, wherein the bacteria strain is Lactobacillus bulgaricus LB 1 deposited with the CNCM, Collection Nationale de Cultures de Microorganismes, Institut Pasteur, under the accession number I-1664.

6. The biologically pure strain of claim 1, wherein the bacteria strain is Lactobacillus bulgaricus LB 3 deposited with the CNCM, Collection Nationale de Cultures de Microorganismes, Institut Pasteur, under the accession number I-1665.

7. The biologically pure strain of claim 1, wherein the bacteria strain is Lactobacillus bulgaricus LB 7 deposited with the CNCM, Collection Nationale de Cultures de Microorganismes, Institut Pasteur, under the accession number I-1666.

8. The biologically pure strain of claim 1, wherein the bacteria strain is Lactobacillus bulgaricus LB 77 deposited with the CNCM, Collection Nationale de Cultures de Microorganismes, Institut Pasteur, under the accession number I-1667.

9. The biologically pure strain of claim 1, wherein the bacteria strain has a 7α-dehydroxylase activity of less than 25%.

10. The biologically pure strain of claim 1, wherein the bacteria strain has a bile acid deconjugation activity of less than 25%.

11. The biologically pure strain of claim 1, wherein the bacteria strain has a 7α-dehydroxylase activity of less than 25% and a bile acid deconjugation activity of less than 50%.

* * * * *